US00PP22053P3

(12) United States Plant Patent

Klemm et al.

(10) Patent No.: US PP22,053 P3

(45) Date of Patent: Aug. 2, 2011

(54) *PELARGONIUM* PLANT NAMED 'KLEPP08212

(50) Latin Name: *Pelargonium peltatum*
Varietal Denomination: KLEPP08212

(75) Inventors: Nils Klemm, Stuttgart (DE); Martin Glawe, Stuttgart (DE)

(73) Assignee: Klemm + Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/383,591

(22) Filed: Mar. 25, 2009

(65) Prior Publication Data

US 2010/0251445 P1 Sep. 30, 2010

(51) Int. Cl.
*A01H 5/00* (2006.01)

(52) U.S. Cl. ..... Plt./332

(58) Field of Classification Search ..... Plt./332
See application file for complete search history.

(56) References Cited

U.S. PATENT DOCUMENTS

PP13,022 P2 * 10/2002 Utecht ..... Plt./332

OTHER PUBLICATIONS

Cassells, A.C. "*Pelargonium peltatum* (ivy-leaf *pelargonium*) Harlequin type: The use of beneficial infective agents and implications for genetic engineering of plants by non-intragrating vectors," ACTA Horticulturae, (1986) No. 182, pp. 229-236.*

Retrieved from website http://www.shootgardeningco.uk/plant/pelargonium-mexicanerin. (1 page total).*

* cited by examiner

*Primary Examiner* — Susan McCormick Ewoldt

(74) *Attorney, Agent, or Firm* — Jondle & Associates, P.C.

(57) ABSTRACT

A new cultivar of *Pelargonium* named 'KLEPP08212' particularly characterized as an ivy *pelargonium* with bi-colored red and light-pink inflorescences, a medium growth habit and branching, an upright and light trailing plant habit, stable inflorescence color; and good tolerance to heat and rain, is disclosed.

1 Drawing Sheet

Genus and species: *Pelargonium peltatum.*
Variety denomination: 'KLEPP08212'.

BACKGROUND OF THE NEW PLANT

The present invention comprises a new and distinct cultivar of *Pelargonium*, botanically known as *Pelargonium peltatum*, and hereinafter referred to by the cultivar name 'KLEPP08212'. 'KLEPP08212' was produced by grafting the *Pelargonium* plant 'Mexicanerin' (unpatented), which contains a unique viroid that causes dichroism, with the *Pelargonium* plant 'Royal Scarlet' (unpatented). 'Mexicanerin' was the rootstock and 'Royal Scarlet' was the scion. The selection criterion for the scion was good red color, zonated leaf, and good growth and branching. After the grafting method, shoot tip cuttings were taken and propagated. The viroid of 'Mexicanerin' passed to the grafting and yielded a new phenotype of bi-colored red-white. There was variation among the plants and selections were made based on color intensity. A single plant selection was subsequently chosen for further evaluation and for asexual propagation via vegetative cuttings. While the mechanism of the viroid is not known, the new trait of dichroism is stable and heritable in that it is passed on to future generations through asexual propagation without the rootstock. The selection criteria used to obtain the final variety was color, growth, and earliness of flowering.

The new cultivar was created in 2006 in Stuttgart, Germany and has been asexually reproduced repeatedly by vegetative cuttings in Stuttgart, Germany over three to four generations. 'KLEPP08212' has been found to retain its distinctive characteristics through successive asexual propagations.

Plant Breeder's Rights for this cultivar have not been applied for. 'KLEPP08212' has not been made publicly available more than one year prior to the filing date of this application.

SUMMARY OF THE INVENTION

The following are the most outstanding and distinguishing characteristics of this new cultivar when grown under normal commercial practices in a greenhouse in Stuttgart, Germany.

1. Ivy *pelargonium* with bi-colored red and light-pink inflorescences;
2. A medium growth habit and good branching;
3. An upright and light trailing plant habit;
4. Stable inflorescence color; and
5. Good tolerance to heat and rain.

DESCRIPTION OF THE PHOTOGRAPH

This new *Pelargonium* plant is illustrated by the accompanying photograph which shows blooms, buds, and foliage of the plant; the colors shown are as true as can be reasonably obtained by conventional photographic procedures.

The photograph is of a plant about 3-months old taken in Spring 2008 and grown from rooted cuttings in a 12-cm pot under greenhouse (glasshouse) in Stuttgart, Germany under conditions which approximate those generally used in commercial practice.

DESCRIPTION OF THE NEW CULTIVAR

The following detailed descriptions set forth the distinctive characteristics of 'KLEPP08212'. The data which define these characteristics were collected from asexual reproductions carried out in Stuttgart, Germany. The plant history was taken on 3-month old plants in 12-cm pots in a greenhouse (glasshouse) in January through April 2008. The plants were pinched once at five weeks. The color readings were determined under natural light. Color references are to the R.H.S. Colour Chart of The Royal Horticultural Society of London (R.H.S.) (2001).

DETAILED BOTANICAL DESCRIPTION

Classification:
- *Family.*—Geraniacaea.
- *Species.*—*Pelargonium peltatum.*
- *Common name.*—*Pelargonium* (Geranium).
- *Denomination.*—'KLEPP08212'.

Parentage: 'KLEPP08212' was produced by grafting the *Pelargonium* plant 'Mexicanerin' (unpatented) with the *Pelargonium* plant 'Royal Scarlet' (unpatented).

Plant:
- *Habit.*—Upright with a lightly trailing growth habit.
- *Height.*—18.0 cm.
- *Spread.*—25.0 cm.
- *Life cycle.*—Spring to autumn.
- *Form.*—Round, bushy.
- *Time to produce a rooted cutting.*—20 days.
- *Earliness of flowering.*—Early.
- *Time to bloom from propagation.*—Approximately 84 days.
- *Lastingness of inflorescence on the plant.*—10 to 14 days.

Stems:
- *Stem color.*—RHS 137B.
- *Pubescence.*—Slightly pubescent.
- *Pubescence color.*—Greenish white.
- *Stem form.*—Round.
- *Diameter.*—0.5 cm to 0.6 cm.
- *Length.*—8.0 cm to 12.0 cm.
- *Internode length.*—1.0 cm to 4.0 cm.

Leaves:
- *Arrangement.*—Alternate.
- *Shape.*—Kidney-shaped, typical of ivy *pelargonium.*
- *Apex.*—Round.
- *Base.*—Closed to open.
- *Margin.*—Entire.
- *Surface appearance* (*both surfaces*).—Dull.
- *Length.*—4.0 cm to 8.0 cm.
- *Width.*—5.0 cm to 8.0 cm.
- *Color.*—Upper surface: RHS 137B Lower surface: RHS 137C.
- *Surface pubescence* (*both surfaces*).—Absent.
- *Petiole.*—Length: 2.0 cm to 7.0 cm Color: RHS 137B.
- *Zonation.*—Medium-strong.
- *Venation pattern.*—Palmate.
- *Venation color.*—RHS 137C.

Inflorescence:
- *Type.*—An umbel composed of 5 to 12 flowers.
- *Flowering habit.*—Continuous.
- *Umbels.*—Length: 4.0 cm to 6.0 cm Diameter: 6.0 cm to 8.0 cm.
- *Individual florets of the umbel.*—Depth: About 1.0 cm Diameter: 4.0 cm to 5.0 cm.

Flower buds:
- *Cluster shape.*—Round-ovate.
- *Length.*—1.0 cm to 4.0 cm.
- *Width.*—1.0 cm to 4.0 cm.
- *Texture.*—Smooth.
- *Bud.*—Shape: Elliptic, shell-shaped Apex: Acute Base: Blunt Margin: Entire, smooth Color: RHS 137B to RHS 137C Size: Length: 1.0 cm to 1.8 cm Width: 0.5 cm to 0.8 cm.

Petals:
- *Quantity per flower.*—9 to 12.
- *Shape.*—Drop-shaped.
- *Apex.*—Round.
- *Base.*—Dull.
- *Margin.*—Entire.
- *Margin.*—RHS 45B.
- *Length.*—2.6 cm.
- *Width.*—1.3 cm.
- *Color of lobes.*—Upper lobes (both surfaces): RHS 45A and RHS 73C Lower lobes (both surfaces): RHS 45B and RHS 73C.
- *Fragrance.*—Absent.

Sepals:
- *Number per flower.*—5.
- *Shape.*—Lanceolate.
- *Apex.*—Acute.
- *Base.*—Obtuse.
- *Margin.*—Entire.
- *Color* (*both surfaces*).—RHS 137B.
- *Length.*—1.8 cm.
- *Width.*—0.4 cm to 0.5 cm.

Pedicel:
- *Length.*—1.8 cm.
- *Diameter.*—0.15 cm.
- *Color.*—RHS 137B.

Peduncle:
- *Length.*—12.0 cm to 16.0 cm.
- *Diameter.*—0.4 cm.
- *Color.*—RHS 137B.
- *Texture.*—Rough.

Reproductive Organs:
- *Stamens.*—Anther length: 0.2 cm Filament length: 0.5 cm to 0.7 cm Filament color: RHS 65D and RHS 66D Pollen amount: Moderate Pollen color: RHS 32A.
- *Pistils.*—Number: 1 Stigma color: RHS 46A Style length: Small, less than 0.5 cm Style color: RHS 137D Ovary arrangement: Central, middle.

Fruit/seed set: None observed.

Disease and Insect Resistance: Good, no specific sensitivity observed to diseases and insects.

COMPARISON WITH PARENTAL AND COMMERCIAL CULTIVARS

'KLEPP08212' differs from the grafting *Pelargonium* parent 'Mexicanerin' (unpatented) in that 'Mexicanerin' has medium-strong growth while 'KLEPP08212' is more compact. 'Mexicanerin' has long internodes while the internodes of 'KLEPP08212' are shorter. The leaf color of 'Mexicanerin' is RHS N137A while the leaf color of 'KLEPP08212' is RHS N137B. Additionally, the zonation of leaves for 'Mexicanerin' is absent or very weak, whereas for 'KLEPP08212', it is medium-strong. The flower characteristics of 'KLEPP08212' differ from 'Mexicanerin' in that the flower petal colors of 'Mexicanerin' are RHS N66A in the margin while 'KLEPP08212' has RHS 45A in the margin. The flower buds of 'Mexicanerin' are small whereas the flower buds of 'KLEPP08212' are thicker. Lastly, the earliness of flowering for the 'Mexicanerin' plant is mid-early, whereas it is early for 'KLEPP08212'.

'KLEPP08212' differs from the grafting *Pelargonium* parent 'Royal Scarlet' (unpatented) in that 'KLEPP08212' has bi-colored red and light-pink inflorescences, while 'Royal Scarlet' (unpatented) has red inflorescences.

'KLEPP08212' differs from the commercial comparison variety 'KLEP01028', also known commercially as 'Royal Candy Cane' (unpatented), in that 'KLEPP08212' has large bi-colored red and light-pink inflorescences, while 'KLEP01028' has smaller purple-red and white inflorescences.

I claim:

1. A new and distinct cultivar of *Pelargonium* plant named 'KLEPP08212' as shown and described herein.

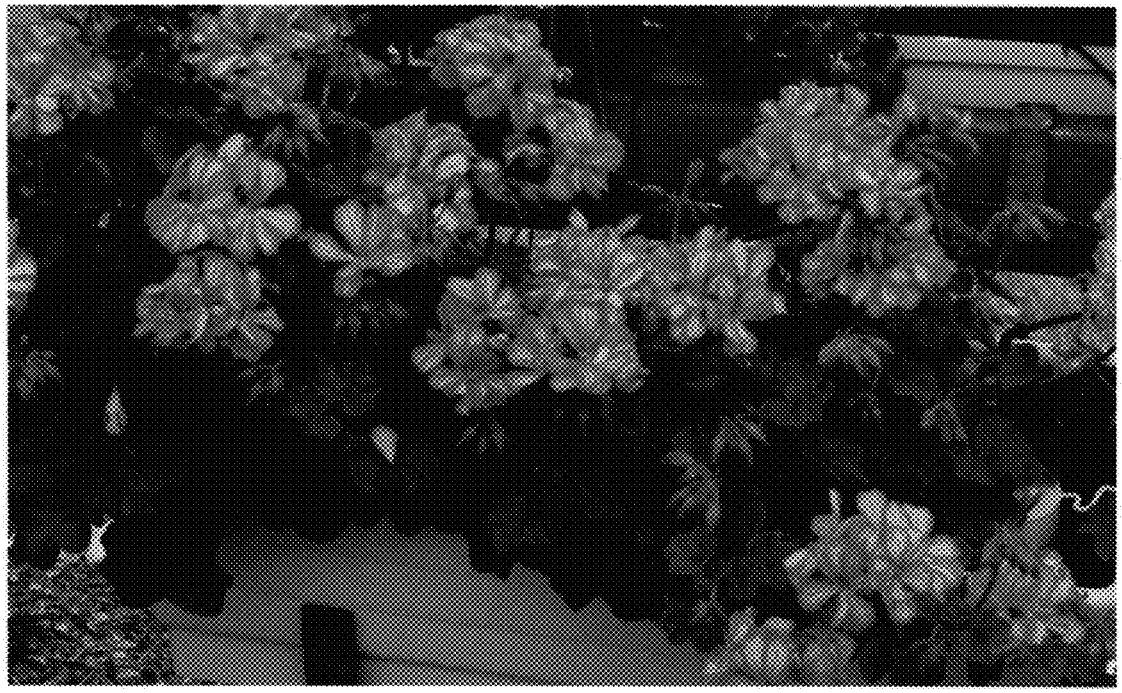

* * * * *